United States Patent [19]

Horn et al.

[11] Patent Number: 5,663,445

[45] Date of Patent: *Sep. 2, 1997

[54] PROCESS FOR THE PREPARATION OF ALCOHOLS OR AMINES

[75] Inventors: Gerhardt Horn, Oberhausen; Carl Dieter Frohning, Wesel, both of Germany

[73] Assignee: Hoechst Aktiengesellschaft, Germany

[*] Notice: The term of this patent shall not extend beyond the expiration date of Pat. No. 5,550,297.

[21] Appl. No.: 453,919

[22] Filed: May 30, 1995

Related U.S. Application Data

[62] Division of Ser. No. 390,375, Feb. 16, 1995, Pat. No. 5,550,297, which is a continuation of Ser. No. 22,685, Mar. 1, 1993, abandoned.

[30] Foreign Application Priority Data

Mar. 4, 1992 [DE] Germany .................. 42 06 750.2

[51] Int. Cl.⁶ .................................................. C07C 209/14
[52] U.S. Cl. ............................................. 564/490; 564/493
[58] Field of Search ........................... 564/493, 490; 502/342, 345

[56] References Cited

U.S. PATENT DOCUMENTS 4,283,581  8/1981  Wilkes .................................. 568/864
5,004,845  4/1991  Bradley et al. ...................... 568/885

Primary Examiner—Brian M. Burn
Attorney, Agent, or Firm—Bierman, Muserlian and Lucas LLP

[57] ABSTRACT

A process for the catalytic preparation of alcohols or amines by reaction of esters, fatty acids, or nitriles with hydrogen at elevated temperature and pressure. The unreduced catalyst contains, per 100 parts by weight of CuO, 40 to 130 parts by weight of ZnO, 2 to 50 parts by weight of $Al_2O_3$, and optionally 0.5 to 8 parts by weight of oxide of Mn, Mo, V, Zr, and/or alkaline earth metal. It has a BET total area of 80 to 175 m²/g of catalyst in the unreduced state, and 75% to 95% of the BET total area is formed by pores having a radius $r_p \leq 15$ nm.

14 Claims, No Drawings

PROCESS FOR THE PREPARATION OF ALCOHOLS OR AMINES

This application is a Divisional of application Ser. No. 08/390,375, filed Feb. 16, 1995, now U.S. Pat. No. 5,550, 297 which was a Continuation of application Ser. No. 08/022,685 filed Mar. 1, 1993, now abandoned. That application claimed priority of foreign Application No. P 42 06 750.2 filed on Mar. 4, 1992, in Germany.

The present invention relates to a process for the preparation of alcohols or amines by reaction of esters, fatty acids or nitriles with hydrogen at elevated temperature and under pressure in the presence of a copper-containing catalyst. The catalyst features a comparatively high BET total area and a particular pore-radius distribution, expressed in terms of the proportion of the BET total area resulting from pores of a particular size. The catalyst is prepared by using a basic precipitant to precipitate from an aqueous solution a copper salt and salts of further elements, to form a coprecipitate, and then washing, drying and calcining the coprecipitate. The catalyst does not contain chemically bound chromium.

BACKGROUND OF THE INVENTION

Copper-containing catalysts are used in industrial processes to a considerable extent; for example, they play an important part in hydrogenation and dehydrogenation processes. In this instance, the feedstock is passed to the fixed catalyst either in the gaseous state (gas-phase operational mode) or in the liquid state (liquid-phase operational mode). The catalyst can also be used in a finely dispersed state as a suspension (suspension operational mode).

Very wide use has been made of catalysts which, in addition to copper, also contain chromium, inter alia for the hydrogenation of esters. These catalysts are known as copper chromite catalysts or Adkins catalysts.

However, the use of Adkins catalysts is not without problems, because their preparation makes use of chromium (VI) compounds which are considered to be carcinogenic and thus, in handling them, appropriate protective measures are required. Furthermore, in the course of their preparation, relatively large quantities of waste waters are produced which are heavily polluted with compounds of copper, chromium (VI), and ammonium salts. Waste waters of this type are undesirable because compounds of both copper and chromium (VI) are highly toxic to micro-organisms and must be removed from the waste water by laborious—and hence expensive—treatment.

Occasional use is also made of copper catalysts containing no chemically bound chromium for the hydrogenation of esters. According to U.S. Pat. No. 4,199,479, supported catalysts containing copper, zinc oxide and, if required, cobalt are suitable for this purpose. EP-B 74,193 describes a process for the hydrogenation of esters in the gas phase by means of a catalyst containing copper and zinc oxide. Chromium-free copper catalysts are also often recommended for other reactions.

Thus, DE-OS 20 56 612 describes a catalyst comprising mixed crystals from the series $(Cu_xZn_y)Al_2(OH)_{16}CO_3.4H_2O$, where x and y can assume numerical values of 0.5 to 5.5 and x plus y equals 6. The mixed crystals are obtained by precipitation at a pH between 4.5 and 5.5, by adding a basic precipitant (for example an aqueous $Na_2CO_3$ solution) to an aqueous solution containing nitrates of copper, zinc and aluminum. The catalyst, which in the non-reduced form contains CuO, ZnO, and $Al_2O_3$, is used in the conversion to methanol of a gas mixture comprising carbon monoxide, carbon dioxide, and hydrogen.

EP 125,689 relates to a catalyst containing CuO, ZnO and $Al_2O_3$, having an atomic ratio Cu:Zn between 2.8 and 3.8 (corresponding to 26.9 to 36.5 parts by weight of ZnO per 100 parts by weight of CuO), and an $Al_2O_3$ fraction from 8% to 12% by weight. $Al_2O_3$ is used in the preeparation as colloidal aluminum hydroxide; Cu and Zn are incorporated in the catalyst by precipitation from metal salt solutions. The catalyst is used for the production of methanol.

It is an object of the present invention to provide a process which makes it possible, not only to produce alcohols by catalytic hydrogenation of esters and fatty acids, but also to produce amines by catalytic hydrogenation of nitriles, with the use of a chromium-free copper catalyst. Furthermore, the process should ensure that the reaction, in particular at elevated temperatures, proceeds with high yield, high selectivity, and substantially avoids the formation of by-products. Also, the results achievable with conventional Adkins catalysts should not only be equalled but, in many cases, distinctly improved. A further advantage is found in the fact that the preparation of the chromium-free copper catalyst circumvents problems which are significant in the preparation of Adkins catalysts; e.g. the handling of carcinogenic chromium (VI) compounds, the production of waste waters containing noxious compounds, and the safe disposal of chromium-containing used catalysts.

SUMMARY OF THE INVENTION

The objects are achieved by a process for the preparation of alcohols or amines by reaction of esters, fatty acids, or nitriles with hydrogen, under pressure and elevated temperature, in the presence of a copper-containing catalyst. The catalyst in the non-reduced state, per 100 parts by weight of CuO, comprises 40 to 130 parts by weight of ZnO, 2° to 50 parts by weight of $Al_2O_3$, and optionally 0.5 to 8 parts by weight of oxide of Mn, Mo, V, Zr, and/or alkaline earth metals. It has a BET total area of 80 to 175 $m^2$ per gram of catalyst in the non-reduced state, 75 to 95% of the BET total area being formed by pores having a radius $r_p \leq 15$ nm.

A further feature of the catalyst according to the invention is its relatively large active copper metal surface area. In the reduced catalyst, the area is 30 to 125, in particular 35 to 100, preferably 40 to 85, $m^2/g$ of Cu and thereby exceeds the active copper metal surface area of corresponding copper chromite catalysts. The method of determination is found in M. J. Juys, P. H. van Oeffelt, W. G. J. Brouwe, A. P. Pijpers and J. J. F. Scholten, Applied Catalysis, 46 (1989), pages 161 to 173.

DETAILED DESCRIPTION OF THE INVENTION

The unreduced catalyst contains, per 100 parts by weight of CuO, from 40 to 130, in particular from 45 to 100, preferably from 45 to 80, parts by weight of ZnO, and from 2 to 50, in particular from 3 to 40, preferably from 4 to 30, most preferably from 4 to 11, parts by weight of $Al_2O_3$. If required, the catalyst may comprise further substances. These include oxides of manganese, molybdenum, vanadium, zirconium, and/or of an alkaline earth metal. Oxides of manganese and/or of alkaline earth metals improve the effectiveness of the catalyst when used for the production of alcohols, oxides of manganese in addition improve the effectiveness of the catalyst when used for the production of amines. Oxides of molybdenum, vanadium and/or zirconium increase the thermostability of the catalyst. Per 100 parts by weight of CuO, their proportion is from 0.5 to 8, particularly from 1 to 6, preferably from 2 to 4, parts by weight, calculated as the oxide(s). Particularly suitable further substances are manganese oxide and/or an alkaline earth metal oxide. Suitable alkaline earth metal oxides include oxides of Mg, Ca, or Ba, in particular Ca oxide or Ba oxide, preferably Ba oxide.

A further feature of the process according to the invention is the comparatively high BET total area of the catalyst. The area is from 80 to 175, in particular from 85 to 160, preferably from 90 to 155, m$^2$/g of catalyst in the non-reduced state. The BET total area is the area measured by adsorption of nitrogen according to the method of Brunauer, Emmett and Teller (BET). The method for determining the BET total area is described in J. Amer. Chem. Soc., 60, (1938) 309.

An additional feature of the catalyst used according to the invention is a particular pore-radius distribution, expressed in terms of a high proportion of the BET total area which is formed by pores having a radius $r_p \leq 15$ nm (150Å). Their proportion is from 75% to 95%, in particular from 80% to 92%, preferably from 84% to 90%, of the BET total area. From 50% to 85%, in particular from 60% to 80%, of the BET total area is formed by pores having a radius $r^p \leq 9$ nm (90Å). The pores whose radii $r_p$ are between 9 and 15 nm constitute 5% to 45%, in particular from 15% to 40%, preferably from 18% to 30% of the BET total area. It should again be noted that the foregoing data regarding the BET total area in each case relates to the catalyst in the non-reduced form. The pore radii are determined by evaluation of the desorption isotherms with the aid of the Kelvin equation according to C. Pierce, J. Phys. Chem. 57, (1953) 149. The data regarding the pore radii also relates to the non-reduced catalyst. If required, the catalyst may, in addition to the components already mentioned, include a support. It comprises 2 to 80, in particular 4 to 60, preferably 5 to 35, parts by weight of the support per 100 parts by weight of CuO. The support may comprise conventional water-insoluble materials. Suitable support materials are $SiO_2$, kieselguhr, silica gel, and $Al_2O_3$, in particular $Al_2O_3$.

The catalyst in reduced form, per 100 parts by weight of Cu, comprises from 48 to 163, in particular from 56 to 125, preferably from 56 to 100, parts by weight of ZnO; from 2.4 to 63, in particular from 3.7 to 50, preferably from 5.0 to 37.5, most preferably from 5 to 13.8, parts by weight of $Al_2O_3$; and, where appropriate, from 0.6 to 10, in particular from 1.2 to 7.5, preferably from 2.4 to 5.0, parts by weight of oxides of Mn, Mo, V, Zr and/or alkaline earth metal.

The preparation of the chromium-free copper catalyst will now be described in more detail. The starting material is an aqueous solution containing salts of copper, zinc, aluminum and, when appropriate, of Mn, Mo, V, Zr, and/or alkaline earth metals. This solution, also designated below as mixed salt solution, contains 10 g to 100 g of Cu/liter, 10 g to 50 g of Zn/liter and Al corresponding to 2 g to 80 g of $Al_2O_3$/liter. If required, the mixed salt solution additionally contains from 3 g to 80 g of Mn, Mo, V, Zr, and/or alkaline earth metal per liter, calculated as the corresponding oxide (s).

The mixed salt solution is prepared by dissolving water-soluble salts of the above-mentioned elements in water. Nitrates have proven to be particularly useful for this purpose. It is advisable to set the pH of the mixed salt solution at less than 4.0, adding acid if required. The precipitant used is an aqueous solution of a basic compound, usually an aqueous alkali metal carbonate or alkali metal hydrogen carbonate solution.

To ensure as complete a precipitation as possible, and to obtain, at the same time, a particularly homogeneous coprecipitate, the basic compound is used in stoichiometric excess. The mixed salt solution and the precipitant, initially separate from one another, are simultaneously and comparatively slowly brought together, continuously or batchwise, with vigorous mixing to form the coprecipitate. The precipitation time should be at least 10 minutes. During precipitation, a constant pH of 6.5 to 8.5, in particular from 7.6 to 8.0, is maintained. Fluctuations of the pH should be kept as low as possible. The precipitation is carried out at constant temperatures above 70° C., in particular from 75° to 95° C. After the precipitation, the coprecipitate is separated from the mother liquor and is carefully washed. In general it is sufficient to maintain, during the washing process, a temperature from 55° to 85°, in particular from 60° to 75° C., and to use from 5 kg to 50 kg of wash water per kg of coprecipitate. The duration of the washing process must be sufficiently long, i.e at least 60 minutes. It has proven sufficient to dry the coprecipitate at temperatures of 50° to 120° C., until a residual moisture content of approximately 2% to 25% by weight, based on the dried coprecipitate, is achieved.

The subsequent calcination takes place at from 250° to 450° C., over a period 3 to 10 hours. The calcined catalyst can either be used in powdered form, directly for suspension hydrogenations or, after shaping, such as tableting or pelleting, as a fixed catalyst.

The process according to the invention is suitable, on the one hand, for the production of alcohols by hydrogenation of the corresponding esters or fatty acids and, on the other hand, for the production of amines by hydrogenation of nitriles. The feedstock materials need not meet any particular requirements, for ecxample with regard to composition or purity. They can be used in the form of the generally available technical grades. Even feedstock materials which, because of particular impurities such as sulfur-containing compounds, are regarded as being difficult to hydrogenate, can be used successfully in the process according to the invention.

The process according to the invention requires somewhat different reaction conditions for the production of alcohols, compared to the production of amines. If alcohols are to be produced, the corresponding esters or fatty acids are reacted at from 200° to 350°, in particular at from 220° to 330°, preferably at from 230° to 320° C. The pressure is usually from 15 to 40, in particular from 18 to 35, preferably from 20 to 32 MPa.

The feedstock materials used are esters of carboxylic acids having from 2 to 30 carbon atoms, in particular of naturally occurring carboxylic acids, having from 8 to 30, preferably from 10 to 24, most preferably from 12 to 22, carbon atoms. These include esters which are formed from the above-mentioned carboxylic acids and monohydric alcohols having 1 to 4 carbon atoms on the one hand, and polyhydric alcohols having 2 to 6 carbon atoms on the other hand. Of particular industrial significance are the methyl and butyl esters of the above-mentioned carboxylic acids. Examples of suitable esters are methyl oleate, and ester mixtures of tallow fatty acid, palm oil acid, palm kernel oil acid, and coconut oil acid, in particular the methyl esters thereof.

Another possible feedstock material comprises fatty acids. The fatty acids contain from 8 to 30, in particular from 10 to 24, preferably from 12 to 22, carbon atoms. They can be saturated, singly unsaturated, or multiply unsaturated. Examples of suitable fatty acids are oleic acid, tallow fatty acid, palm oil acid, palm kernel oil acid, and coconut oil acid.

For the production of amines, nitriles are usually reacted under somewhat milder conditions than the esters and fatty acids. Temperatures of from 160° to 250° in particular of from 190° to 240° C., preferably of from 210° to 230° C., and pressures of from 0.5 to 10, in particular of from 1.0 to 5.0, preferably of from 1.2 to 3.0 MPa, constitute suitable reaction conditions. Nitriles having from 4 to 30, in particular from 8 to 24, preferably from 10 to 22, carbon atoms can be converted in this manner into the corresponding amines. Examples of suitable nitriles are propionitrile, butyronitrfle, valeronitrile, capronitrile, caprylonitrile, lauronitrile, myristonitrile, palmitonitrile, oleonitrile, stearonitrile, and alkylaminonitriles having 2 to 6 carbon atoms in the alkyl chain; as well as aliphatic, cycloaliphatic, and aromatic dinitriles, such as adiponitrile and isophorone dinitrile.

EXAMPLE 1

Hydrogenation of a fatty acid methyl ester mixture containing predominantly methyl oleate The feedstock used is a fatty acid methyl ester mixture consisting predominantly of methyl oleate (Estol 1400, commercially available from Unilever) which has the following composition (determined by gas-chromatographic analysis):

| | |
|---|---|
| $C_{12}$-acid methyl ester | 0.5% by weight |
| $C_{14}$-acid methyl ester | 4.5% by weight |
| $C_{16}$-acid methyl ester | 11.5% by weight |
| $C_{18}$-acid methyl ester | approx. 81.0% by weight |
| $C_{20}$-acid methyl ester | approx. 0.8% by weight |
| (remaining components not identified) | |

The fatty acid methyl ester mixture, because of its sulfur content (25 ppm by weight) is difficult to hydrogenate.

The catalyst I required for the reaction is prepared as follows:

1800 g $Cu(NO_3)_2.H_2O$, 1130 g $Zn(NO_3)_2.6H_2O$, and 370 g $Al(NO_3)_3.9H_2O$ are dissolved in 7 l water, to form a mixed salt solution. The basic precipitant used is an aqueous $Na_2CO_3$ solution (1550 g $Na_2CO_3$ solved in 14 l distilled water). The mixed salt solution and the basic precipitant are separately heated to 80° C., separate streams of the two reactants brought together simultaneously with stirring, the resultant mixture is filtered and the coprecipitate formed is washed with hot water. The washed filter cake is dried to a final moisture content of $\leq 5\%$ by weight, based on the catalyst mass, and is subsequently calcined in a nitrogen stream at 380° C.

The calcined catalyst I used for the reaction contains, in its unreduced state, 59.2% by weight of CuO (corresponding to 47.3% by weight of Cu) and, per 100 parts by weight of CuO; 52.4 parts by weight of ZnO and 8.4 parts by weight of $Al_2O_3$ (This corresponds in % by weight to 59.2% CuO, 31.0% zno, 5.0% $A_2O_3$, the rest being $CO_2$, $H_2O$ and oxygen.) The BET total area is 126 $m^2/g$ of catalyst in the unreduced state. 89% of the BET total area is formed by pores having a radius $r_p \leq 15$ nm, and 76% of the BET total area is formed by pores having a radius $r_p \leq 9$ nm. The copper metal area of the reduced catalyst is 78 $m^2/g$ of Cu.

A 1 liter autoclave, equipped with an oscillating magnetic stirrer, is charged, while ate is excluded, with 400 g of the previously described fatty acid methyl ester mixture and 4 g of catalyst I. The vessel is then pressurized with hydrogen to 18 MPa and, with stirring (100 strokes per minute), is heated to 250° C. in 50 minutes. During heating, the pressure rises to 25 MPa. By pressurizing repeatedly with hydrogen, the pressure is kept constant at 25 MPa. After a reaction time of 125 minutes, hydrogen is not longer taken up; the reaction is complete. The autoclave is depressurized and cooled down.

COMPARATIVE EXAMPLES 1 to 5

Hydrogenation of a fatty acid methyl ester mixture containing predominantly methyl oleate The same procedure is followed as in Example 1, but in each case, 4 g of a commercially available catalyst are used. The reaction is halted after 125 minutes. At that time, the hydrogen uptake has not yet finished.

The following catalysts are used:

Catalyst A in Comparative Example 1:

A copper chromite catalyst containing 42% by weight of Cu and 26% by weight of Cr. The BET total area is 50 $m^2$ per gram of catalyst.

Catalyst B in Comparative Example 2:

A copper chromite catalyst containing 36% by weight of Cu, 32% by weight of Cr, 2.2% by weight of Ba and 2.4% by weight of Mn. The BET total area is 30 $m^2$ per gram of catalyst.

Catalyst C in Comparative Example 3:

A copper chromite catalyst containing 36% by weight of Cu, 32% by weight of Cr, 2.2% by weight of Ba and 2.4% by weight of Mn. The BET total are is 65 $m^2$ per gram of catalyst.

Catalyst D in Comparative Example 4:

A copper chromite catalyst containing 36% by weight of Cu, 33% by weight of Cr and 3% by weight of Mn. The BET total area is 55 $m^2$ per gram of catalyst.

Catalyst E in Comparative Example 5:

A copper chromite catalyst containing approximately 47% by weight of CuO, approximately 49% by weight of $Cr_2O_3$ and approximately 4% by weight of $MnO_2$. The BET total area is 30 $m^2$ per gram of catalyst.

EXAMPLE 2

Hydrogenation of a fatty acid methyl ester mixture containing predominantly methyl oleate The same procedure is followed as in Example 1, except that the reaction is carried out at 300° C. and 27 MPa. Hydrogenation is complete after only 45 minutes.

COMPARATIVE EXAMPLE 6

Hydrogenation of a fatty acid methyl ester mixture containing predominantly methyl oleate The same procedure is followed as in Example 2,except that 4 g of catalyst B are used. However, hydrogen uptake is only complete after 90 minutes.

The results of Examples 1 and 2 and of Comparative Examples 1 to 6 are summarized in the following Table 1.

TABLE 1

|  | Example | Comparative Examples | | | | | Example | Comparative Examples |
| --- | --- | --- | --- | --- | --- | --- | --- | --- |
|  | 1 | 1 | 2 | 3 | 4 | 5 | 2 | 6 |
| Catalyst | I | A | B | C | D | E | I | B |
| Temperature (°C.) | 250 | 250 | 250 | 250 | 250 | 250 | 300 | 300 |
| Pressure (MPa) | 25 | 25 | 25 | 25 | 25 | 25 | 27 | 27 |
| Reaction time (min) | 125 | 125 | 125 | 125 | 125 | 125 | 45 | 90 |
| Composition of the reaction product (in % by weight) | | | | | | | | |
| $C_{12}$-alcohol | 0.5 | 0.3 | 0.4 | 0.4 | 0.3 | 0.3 | 0.5 | 0.5 |
| $C_{14}$-alcohol | 4.3 | 2.9 | 1.4 | 1.3 | 1.8 | 1.0 | 4.5 | 3.5 |
| $C_{16}$-acid methyl ester | 0.2 | 10.5 | 9.1 | 9.3 | 7.1 | 8.7 | 0.1 | 1.3 |
| $C_{16}$-alcohol | 11.2 | 0.7 | 2.0 | 2.6 | 3.9 | 1.9 | 10.8 | 10.1 |
| $C_{18}$-acid methyl ester | 1.3 | 74.9 | 66.0 | 59.6 | 57.2 | 67.7 | 1.0 | 2.8 |
| $C_{18}$-alcohol | 78.2 | 3.7 | 13.0 | 6.5 | 22.6 | 11.4 | 78.7 | 75.5 |
| $C_{20}$-alcohol | 0.6 | 0.2 | 0.3 | 0.2 | 0.1 | 0.3 | 0.5 | 0.3 |

EXAMPLE 3

Hydrogenation of a fatty acid methyl ester mixture containing predominantly methyl laurate and methyl myristate The feedstock used is a fatty acid methyl ester mixture (coconut methyl ester), consisting predominantly of methyl laurate and of methyl myristate, which has the following composition (determined by gas-chromatographic analysis):

| | |
| --- | --- |
| $C_{10}/C_{11}$-acid methyl ester | 0.7% by weight |
| $C_{12}$-acid methyl ester | approx. 55.0% by weight |
| $C_{14}$-acid methyl ester | approx. 21.0% by weight |
| $C_{16}$-acid methyl ester | approx. 10.0% by weight |
| $C_{18}$-acid methyl ester | approx. 13.0% by weight |

The catalyst II required for the reaction is prepared in an analogous manner to that of catalyst I described in Example 1.

The calcined catalyst II, in the unreduced state, contains 58.6% by weight of CuO (corresponding to 46.9% by weight of Cu) and, per 100 parts by weight of CuO, 50.2% parts by weight of ZnO, 8.0 parts by weight of $Al_2O_3$, and 2.6 parts by weight of BaO.

The BET total area is 118 $m^2/g$ of catalyst in the unreduced state. 87% of the BET total area is formed by pores having a radius $r_p \leq 15$ nm, and 74% of the BET total area is formed by pores having a radius $r_p \leq 9$ nm. The copper metal surface area of the reduced catalyst is 74 $m^2/g$ of Cu.

A 1 liter autoclave, equipped with an oscillating magnetic stirrer, is charged, while air is excluded, with 400 g of the previously described fatty acid methyl ester mixture (coconut methyl ester) and 4 g of catalyst II. The vessel is then pressurized with hydrogen to 18 MPa and, with stirring (100 strokes per minute), is heated to 250° C. in 50 minutes. During heating, the pressure rises to 25 MPa. By pressurizing repeatedly with hydrogen, the pressure is kept constant at 25 MPa. After a reaction time of 75 minutes, hydrogen is no longer taken up; the reaction is complete. The autoclave is depressurized and cooled down.

COMPARATIVE EXAMPLES 7 AND 8

Hydrogenation of a fatty acid methyl ester mixture containing predominantly methyl laurate and methyl myristate The same procedure is followed as in Example 3, except that 4 g of catalyst B (Comparative Example 7) and 4 g of catalyst D (Comparative Example 8) are used. However, in both Comparative Examples 7 and 8, the hydrogen uptake does not cease until a reaction time of 135 minutes.

The results of Example 3 and of Comparative Examples 7 and 8 are summarized in the following Table 2.

TABLE 2

|  | Example | Comparative Example | |
| --- | --- | --- | --- |
|  | 3 | 7 | 8 |
| Catalyst | II | B | D |
| Temperature (°C.) | 250 | 250 | 250 |
| Pressure (MPa) | 25 | 25 | 25 |
| Reactio time (min) | 75 | 135 | 135 |
| Composition of the reaction product (in % by weight) | | | |
| $C_{10-11}$-alcohol | 0.7 | 0.4 | 0.5 |
| $C_{12}$-acid methyl ester | 1.0 | 35.3 | 28.6 |
| $C_{12}$-alcohol | ~54 | 20.7 | 25.5 |
| $C_{14}$-acid methyl ester | 0.5 | 14.5 | 12.4 |
| $C_{14}$-alcohol | 20.5 | 6.5 | 8.5 |
| $C_{16}$-acid methyl ester | 0.3 | 7.2 | 6.8 |
| $C_{16}$-alcohol | ~10 | 2.8 | 3.7 |
| $C_{18}$-acid methyl ester | 0.4 | 9.4 | 9.7 |
| $C_{18}$-alcohol | 12.5 | 2.9 | 4.1 |

EXAMPLE 4

Hydrogenation of palm kernel oil acid

The feedstock used is non-esterified palm kernel oil acid having the following characteristics:

Iodine number: 13.0 g $I_2$/100 g
Acid number : 267 mg KOH/g

A 1 liter autoclave, equipped with an oscillating magnetic stirrer is charged, while air is excluded, with 400 g of the previously described palm kernel oil acid and 32 g of catalyst I. The vessel is then pressurized with hydrogen to 18 MPa, with stirring (100 strokes per minute), and is heated to 300° C. in 90 minutes. During heating, the pressure rises to 27 MPa. By pressurizing repeatedly with hydrogen, the pressure is kept constant at 27 MPa. After a reaction time of 100 minutes, hydrogen is no longer taken up; the reaction is complete. The autoclave is depressurized and cooled down.

COMPARATIVE EXAMPLE 9

Hydrogenation of palm kernel oil acid

The same procedure is followed as in Example 4, except that 32 g of a commercially available copper chromite catalyst are used; the catalyst contains 35.5% by weight of Cu, 32.6% by weight of Cr, and 4.2% by weight of Ba (catalyst F).

The results of Example 4 and Comparative Example 9 are summarized in the following Table 3.

TABLE 3

|  | Example 4 | Comparative Example 9 |
|---|---|---|
| Catalyst | I | F |
| Temperature (°C.) | 300 | 300 |
| Pressure (MPa) | 27 | 27 |
| Reaction time (min) | 100 | 100 |
| Characteristics of the reaction product | | |
| Iodine number (g $I_2$/100 g) | 0.12 | 1.9 |
| Acid number (mg KOH/g) | 0.39 | 5.8 |
| Hydroxyl number (mg KOH/g) | 273 | 209 |

EXAMPLE 5

Hydrogenation of a fatty acid nitrile

The feedstock used is tallow fatty acid nitrile having an iodine number of 55.3 g $I_2$/100 g.

A 1 liter autoclave, equipped with an oscillating magnetic stirrer, is charged, while excluding air, with 400 g of tallow fatty acid nitrile and 10 g of catalyst I. The reaction is carried out at 220° C. and 1.5 MPa. After a reaction time of 240 minutes, hydrogen is no longer taken up; the reaction is complete. The autoclave is depressurized and cooled down.

The reaction product contains 63.8% by weight of primary fatty amine, 34.5% by weight of secondary fatty amine and 1.5% by weight of tertiary fatty amine. The residual iodine number is 52.6 g $I_2$/100 g.

While only a limited number of specific embodiments of the present invention have been expressly disclosed it is, nonetheless, to be broadly construed, and not to be limited except by the character of the claims appended hereto.

What we claim is:

1. A process for the hydrogenation of a nitrile to form a corresponding amine, said process comprising a reaction of said nitrile with hydrogen at elevated pressure and elevated temperature, in the presence of a catalyst which contains CuO, said catalyst, in its unreduced state, comprising, per 100 parts of said CuO, 40 to 130 parts by weight of ZnO, 2 to 50 parts by weight of $Al^2O^3$, and having a BET total area of 80 to 175 m$^2$/g, 75% to 95% of said total area constituting pores having radii $r_p \leq 15$ nm.

2. The process of claim 1 wherein said elevated temperature is 160° to 250° C. and said elevated pressure is 0.5 to 10 MPa.

3. The process of claim 2 wherein said elevated temperature is 210° to 230° C. and said elevated pressure is 1.2 to 3.0 MPa.

4. The process of claim 1 wherein said catalyst, in its reduced state, has an active copper metal surface area of 30 to 125 m$^2$/g of said copper.

5. The process of claim 4 wherein said surface area is 40 to 85 m$^2$/g of said copper.

6. The process of claim 1 wherein said catalyst, in said unreduced state, per 100 parts by weight of said CuO, comprises 45 to 80 parts by weight of ZnO and 4 to 11 parts by weight of $Al_2O_3$.

7. The process of claim 1 wherein said total area is 90 to 155 m$^2$/g of said catalyst in said unreduced state.

8. The process of claim 1 wherein 84% to 90% of said total area constitutes said pores having radii $r_p \leq 15$ nm.

9. The process of claim 1 wherein said catalyst per 100 parts by weight of CuO, contains 4 to 60 parts by weight of a water-insoluble support.

10. The process of claim 1 wherein said support is selected from the group consisting of kieselguhr, silica gel, $SiO_2Al_2O_3$, and mixtures thereof.

11. The process of claim 1 wherein said support is $SiO_2$ and/or $Al_2O_3$.

12. A process for the hydrogenation of a nitrile having 4 to 30 carbon atoms, to form a corresponding amine, said process comprising a reaction of said nitrile with hydrogen at elevated pressure and elevated temperature in the presence of a catalyst which contains CuO, said catalyst, in its unreduced state, comprising, per 100 parts of said CuO, 40 to 130 parts by weight of ZnO, and 2 to 50 parts by weight of $Al_2O_3$, and having a BET total area of 80 to 175 m$^2$/g, 75% to 95% of said total area constituting pores having radii $r_p \leq 15$ nm.

13. The process of claim 12 wherein said nitrile has 8 to 24 carbon atoms.

14. The process of claim 13 wherein said nitrile has 10 to 22 carbon atoms.

* * * * *